United States Patent [19]

Hahn et al.

[11] Patent Number: 4,576,159
[45] Date of Patent: Mar. 18, 1986

[54] GAS MIXING AND FLOW SMOOTHING APPARATUS

[75] Inventors: Clive E. W. Hahn, Oxon; Eileen Palayiwa, Oxford; David J. Lindsay-Scott, Oxon; Basil R. Sugg, Oxford; Paul J. Tyrrell, Oxon, all of England

[73] Assignee: Penlon Limited, England

[21] Appl. No.: 582,912

[22] Filed: Feb. 23, 1984

[30] Foreign Application Priority Data

Feb. 24, 1983 [GB] United Kingdom ............... 8305117

[51] Int. Cl.⁴ .......................................... A61M 16/00
[52] U.S. Cl. ........................ 128/203.14; 128/205.24; 128/205.16; 128/205.23; 128/203.25; 137/606; 137/896; 138/31; 138/46
[58] Field of Search ............... 128/201.27, 201.28, 128/203.12, 203.25, 205.24, 204.21, 204.24, 204.25, 203.14, 205.16, 205.23; 137/606, 607, 896, 897, 898; 138/26, 30, 31, 46

[56] References Cited

U.S. PATENT DOCUMENTS

| | | | |
|---|---|---|---|
| 2,904,076 | 9/1959 | Engel et al. | 138/26 |
| 3,487,855 | 1/1970 | Lantenberger, Jr. | 138/31 |
| 4,026,283 | 5/1977 | Banjavich et al. | 128/201.27 |
| 4,137,912 | 2/1979 | O'Neill | 128/201.27 |

Primary Examiner—Henry J. Recla
Attorney, Agent, or Firm—Bacon & Thomas

[57] ABSTRACT

Gas mixing and flow smoothing apparatus for use in for example an anaesthesia system comprises a mixing chamber (8) which receives the flow of two or more gases via control valves (6,7). The mixing chamber (8) is adapted to absorb fluctuations in the pressure of the gases therein through the provision of for example a spring-loaded piston (not shown) which forms one wall of the chamber, and the pressure at the outlet (30) from the chamber (8) is maintained at a substantially constant pressure by means of a valve (9). If desired, further attenuation of the gas flow may be achieved through the provision of a second series arrangement of surge damper (11) and back pressure valve (10) located downstream from the valve (9).

20 Claims, 6 Drawing Figures

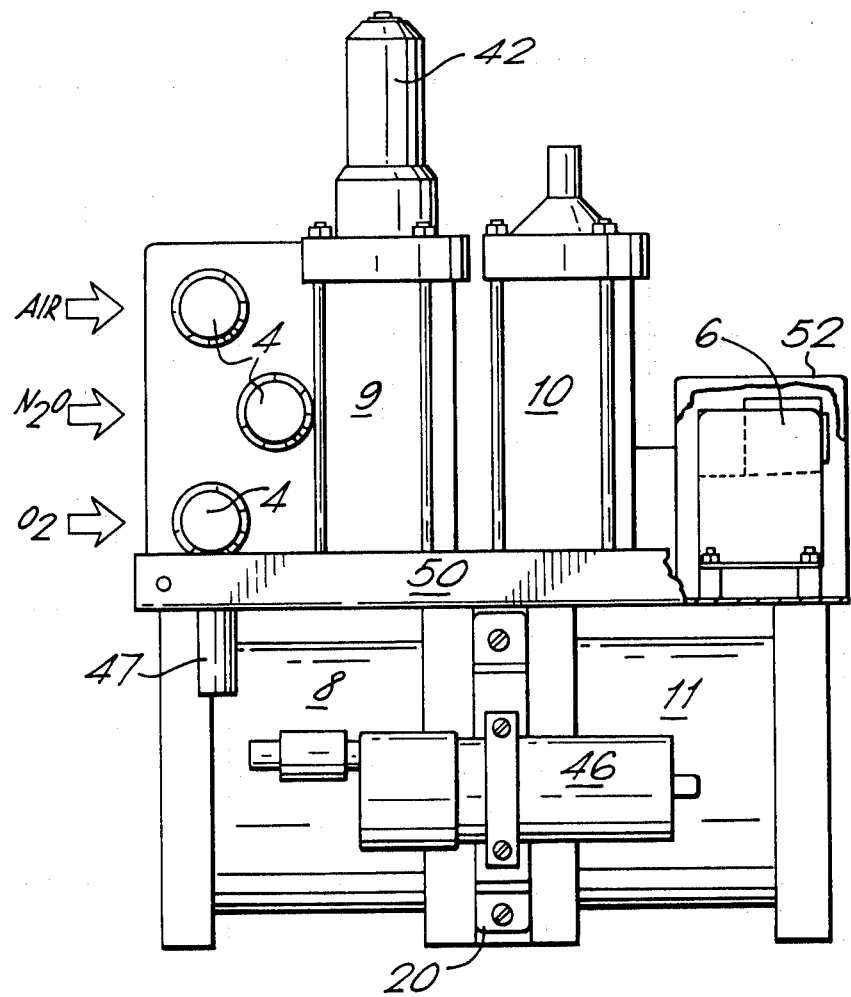

GAS MIXING AND FLOW SMOOTHING APPARATUS

This invention relates to apparatus for the mixing and smoothing of gas flows and is particularly concerned with apparatus adapted to produce a smooth and regulated flow of two or more mixed gases for use in the medical field of anaesthesia apparatus.

In conventional anaesthesia apparatus a patient is supplied with a mixture of at least two gases, for example, oxygen and air or nitrous oxide, the mixed gases being dosed with vapourised anaesthetic drugs. With such apparatus it is essential that the proportions of the various gases in the mixture supplied to the patient are precisely regulated and furthermore a particularly smooth overall flow is required. It has been proposed to control the relative proportions of the constituent gases by means of a pulsed control valve in the supply line of each gas, the frequency or period of the valve pulses regulating the flow rate of the gas. Such an arrangement is advantageous in that the proportions of the gases may be set very accurately within a wide range of possible values. Furthermore, the pulsed valves, being solenoid controlled, are inherently suitable for use with electronic control circuitry. However, a major drawback with such an arrangement is that the resulting flow of the mixed gases is heavily pulsed both in terms of its instantaneous flow rate and in terms of the instantaneous relative proportions of its constituents. Such fluctuations are clearly undesirable and can be harmful to the patient.

Viewed from a first aspect the invention provides apparatus for mixing and smoothing the flow of two or more gases, comprising a mixing chamber with at least two inlet ducts and an outlet duct, the mixing chamber being adapted to absorb fluctuations in the pressure of the gases therein, and a valve connected downstream of the chamber adapted to maintain a substantially constant pressure at said chamber outlet duct.

The series arrangement of a mixing chamber which acts as a surge damper and a substantially constant back pressure valve is such that any fluctuations in the flow of the inlet gases are attenuated and a substantially smooth flow of the mixed gases may be obtained from an outlet of the back pressure valve. Apparatus in accordance with the invention is therefore particularly suitable for mixing and smoothing regulated flows of different gases produced by pulsed control valves in an anaesthesia system.

In a preferred embodiment, the mixing chamber is cylindrical in shape, and the inlet ducts are arranged such that the gases enter the chamber tangentially in opposite directions. In this way the inlet flows tend to produce toroidal currents within the chamber which are in opposed senses, and this increases the efficiency of the mixing of the gases therefore minimising instantaneous variations in the relative proportions of the constituent gases in the outlet flow.

The mixing chamber is preferably adapted to absorb fluctuations in gas pressure through the provision of a spring loaded piston which defines one wall of the chamber and which is outwardly displaceable in response to increases in gas pressure within the chamber. Sealing means for the piston may take any convenient form, for example sliding O-rings disposed between the piston and the chamber wall. Alternatively the gas pressure may act on the piston through a flexible rolling diaphragm seal which is secured across the chamber adjacent to the piston and prevents gases escaping around the periphery of the piston.

In a particularly advantageous embodiment, the constant back pressure valve is a variable orifice valve adapted to produce a substantially constant back pressure over a wide range of gas flow rates. Thus, a required operational gas pressure within the mixing chamber for efficient flow smoothing is maintained over a wide range of flow rates, and this is particularly important in an anaesthesia system where the required total flow of gases delivered to a patient might vary considerably. A preferred embodiment of back pressure valve includes a gravity loaded plunger or float slidably mounted in a vertically disposed tapered passage. In use the flow of mixed gases from the mixing chamber outlet is passed upwardly through the passage such that the plunger is forced upwardly until an equilibrium position is reached where the back pressure is equal to the weight of the plunger assembly. Preferably the plunger includes angled slots or channels around its periphery such that the passage of gas produces a rotational torque on the plunger. The resulting rotation of the plunger reduces the influence of friction and mechanical shock within the valve. A preferred embodiment of back pressure valve has been found to produce a substantially constant back pressure over flow rates varying between two and eighteen liters per minute.

Where particularly efficient attenuation is required the apparatus may include a second surge damper and constant back pressure valve arranged in series downstream of the first constant back pressure valve. The second surge damper may be of similar construction to the mixing chamber and thus preferably comprises an enclosed cylindrical chamber one wall of which is defined by a spring loaded damping piston. In a preferred embodiment, the mixing chamber and second surge damper are secured together in back-to-back relationship with a central connecting plate disposed therebetween. In this embodiment, the gases may conveniently be transmitted to and from the chambers via conduits formed in the connecting plate. The back-to-back configuration of the two cylindrical chambers provides a particularly compact unit.

Clearly the overall attenuation of a variable or pulsed flow is greatly increased through the use of two surge damper and back pressure valve combinations arranged in series. If for example the attenuation factor of each combination is 80%, then the first combination would transmit to the second combination 20% of any pulse entering the apparatus; the second combination however would reduce this transmission to 20% of 20%, that is 4% of the original pulse at the inlet.

In many instances it may be desirable to measure the rate of gas flow through the apparatus, and therefore a preferred embodiment of the invention includes a metering device for measuring the flow. The preferred form of constant back pressure value discussed above may conveniently be adapted for flow measurement, since the vertical displacement of the float or plunger thereof is related to the flow rate. In a preferred embodiment, a ferromagnetic rod is secured to and extends upwardly of the plunger assembly and is movable therewith. Displacement is measured by means of an assembly of inductance coils which surround the rod, changes in inductance being indicative of vertical movements of the plunger. Where fluctuating flows occur through the valve, an integral value of inductance may be obtained such that the average flow rate over a certain period of time is measured. This reduces the possibility of errors arising due to, for example, the plunger sticking within the passage. The preferred form of flow meter is particularly suitable for use with electronic control circuitry adapted continuously to monitor the gas flow rate through the apparatus.

Viewed from a second aspect the invention provides a method of mixing and smoothing the flow of two or more gases comprising introducing the gases into an enclosed mixing chamber, the mixing chamber being adapted to absorb fluctuations in the pressure of the gases therein, and passing the mixed gases through a valve located downstream of the mixing chamber adapted to maintain a subtantially constant pressure at the outlet of said chamber.

As mentioned above, the apparatus and method in accordance with the first and second aspects of the invention are particularly suited for the supply of mixed gases to a patient in an anaesthesia system. Thus, viewed from a third aspect the invention provides gas supply apparatus for an anaesthesia system comprising two or more pulsed valves adapted to produce regulated flows of two or more gases, a mixing chamber downstream of the valves in which the gases are mixed, surge damper means and back pressure valve means for attenuating pulses in the mixed gas flow, means for directing a controlled proportion of the total gas flow to anaesthetic drug dosing means, and a second mixing chamber for remixing the dosed gases with the main gas flow.

Preferably the outlet orifices or jets of the pulsed valves are mounted so as to be in good thermal communication with one another. This is important to minimise the effect of relative thermal expansion or contraction of the orifices which can render the relative flow rates of the two gases inaccurate. This problem is significant where only a small percentage of one gas is required and thus the cooling effect resulting from the gas flow through one valve is very much less than that occuring from the gas flow through the other valve. In the preferred configuration of back-to-back cylindrical surge dampers discussed above, the valve jets may conveniently be disposed in suitable orifices formed in the common connecting plate between the two cylinders.

In a preferred form of the invention, the various components of the system are arranged on a common mounting plate or tray thus forming a compact unit. Through the use of the preferred inductance flow meter together with solenoid controlled pulsed valves, the system lends itself to electronic control and monitoring by a microprocessor.

A preferred embodiment of the invention will now be described, by way of example only, with reference to the accompanying drawings, wherein:

FIG. 6 is a side elevation of the apparatus shown in FIG. 5.

Figure 1:
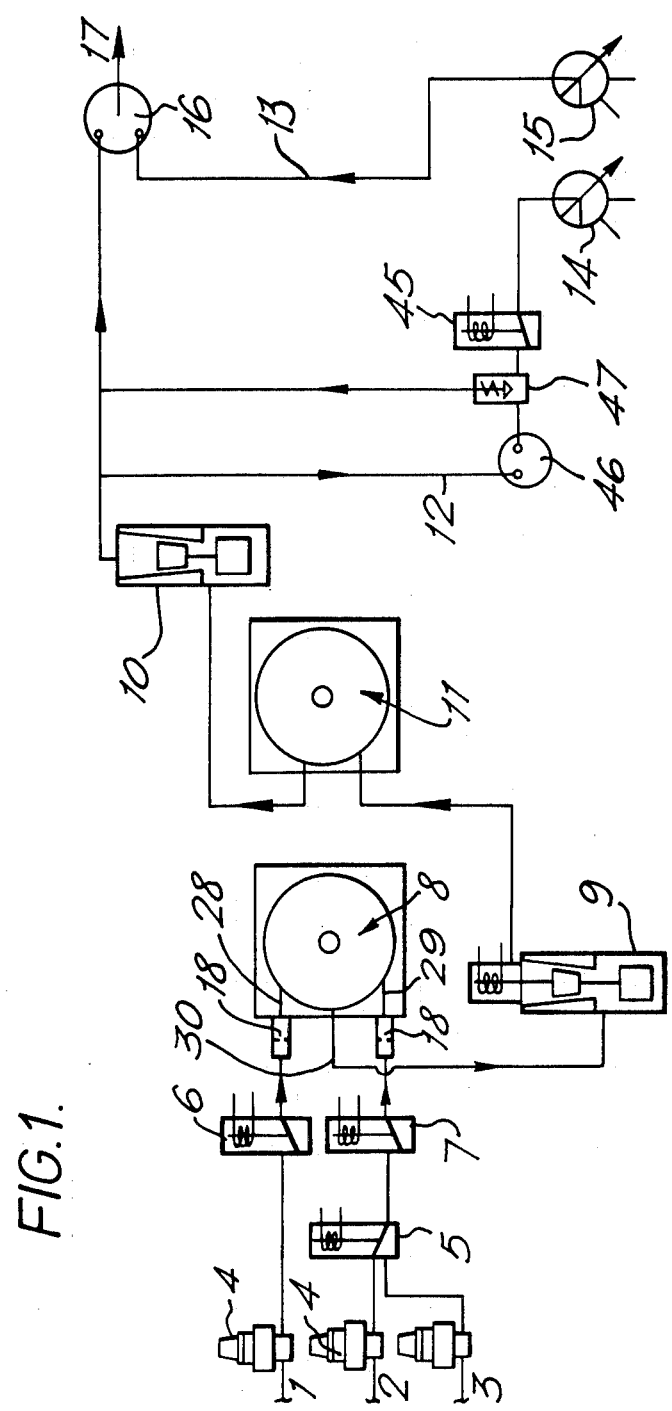
FIG. 1 is a schematic diagram illustrating gas supply apparatus for an anaesthesia system.

Referring firstly to FIG. 1, gas supply apparatus for an anaesthesia system includes three inlet ducts 1, 2, 3 which in use are connected respectively to pressurised supplies of oxygen, nitrous oxide and air at pressures in the order of 60 p.s.i. The inlets 1,2,3 lead via pressure regulating valves 4 and solenoid controlled valves 5,6,7 to a mixing and flow smoothing apparatus comprising a combined mixing chamber and surge damper 8, two constant back pressure valves 9,10 and a second surge damper, all arranged in series as shown. Downstream of the second back pressure valve 10, a controlled proportion of the gas flow is directed in a manner to be described via a line 12 to a selector valve 14 which in use is connected to a number of vapourisers (not shown) for dosing the mixed gases with appropriate anaesthetic drugs. A selector valve 15 receives the dosed gases which are returned to the main flow via a line 13 and a second mixing chamber 16. The anaesthetic gases for supply to a patient leave the chamber 16 via an outlet duct 17.

In the illustrated embodiment, oxygen from the inlet 1 is mixed with either air or nitrous oxide, although clearly additional inlets might be provided for alternative gases. The solenoid controlled valve 5 selects whether nitrous oxide from the inlet 2 or air from the inlet 3 enters the system. The solenoid controlled valves 6 and 7 are pulsed metering valves adapted to regulate precisely the flow rates of the gases to required mean values such that the quantity of each gas supplied to a patient is accurately controlled. The gas pressure upstream of the valves 6, 7 is held constant by the regulating valves 4, and the flow rates through the metering valves 6,7 is therefore dependent upon the duration of the open periods of the valves 6,7. In a preferred arrangement, control circuitry (not shown) for the apparatus includes means for generating a high frequency fundamental signal and the open pulses of each valve consist of an integral multiple of the period of this signal. In this way the length of the open periods of the valves 6,7 and thus the flow rates may be incrementally varied with a high degree of accuracy.

The metering valves 6,7 produce pulsed gas flows which are introduced into the combined mixing chamber and surge damper 8 via respective valve nozzles or jet 18 having small orifices which may be adjustable to compensate for differences in density and viscosity of the gases such that the same volume of each gas is passed for a given open period of either valve 6,7. Alternatively the size of the jet orifices may be fixed and gas density and viscosity differences may be compensated for by adjusting the pressure regulating valves 4. As described below, the jets 18 are mounted within a common metal plate and are therefore in mutual thermal contact. Thus relative temperature variations of the jets due to different gas flow rates therethrough are minimised.

Figure 3:
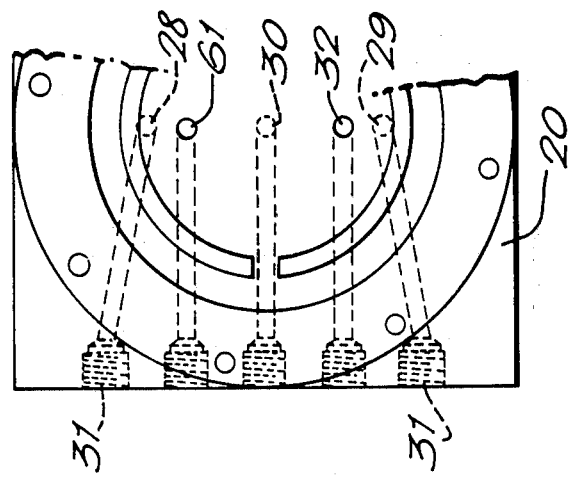
FIG. 3 is a section taken along line III—III in FIG. 2.
Figure 2:
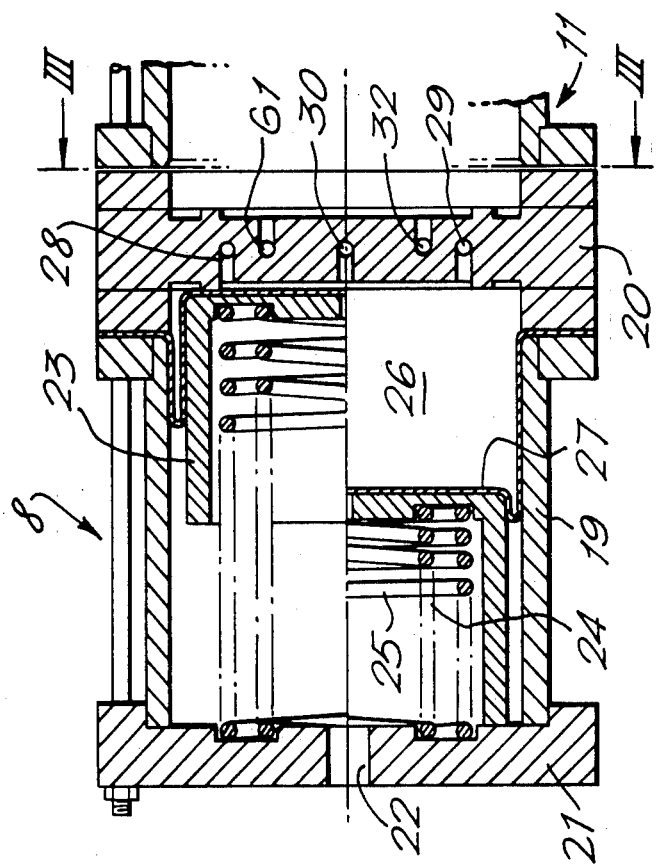
FIG. 2 is a sectional view through a combined mixing chamber and surge damper.

Referring now to FIGS. 2 and 3, the details of the combined mixing chamber and surge damper 8 are illustrated. The chamber includes a cylindrical housing 19 closed at one end by a connecting plate 20 and at the other end by an end plate 21 including an aperture 22 open to the atmosphere. The end plate 21 mounts a piston 23 which is movable against the action of two coil springs 24,25 between the two extreme positions illustrated in FIG. 2. The front face of the piston 23 defines a side wall of an enclosed mixing chamber 26. A perfect seal is ensured by a flexible rolling diaphragm 27 which is secured across the interior of the cylinder 19 and overlies the piston. Formed in the connecting plate 20 are two inlet orifices 28,29 through which the gases to be mixed are introduced into the chamber 26, and a centrally disposed outlet orifice. The jets of the pulsed metering valves 6,7 may conveniently be disposed in enlarged end portions 31 of the inlet orifices 28,29 thereby ensuring mutual thermal contact therebetween. It will be seen that the orifices 28,29 are arranged tangentially and that the two gas flows into the chamber 26 will tend to produce circulating currents in opposite directions; this promotes efficient mixing of the two gases and thus reduces the possibility of instantaneous variations in the relative concentrations of the constituent gases.

The outlet 30 is connected to the valve 9 which is adapted to maintain a substantially constant back pressure over a wide range of flow rates in a manner to be described. The spring loaded piston 23 acts as a surge damper which absorbs increases in gas pressure within the chamber 26 owing to the pulsed inlet flow and thus the series combination of chamber and back pressure valve constitutes a mechanical resistance and compliance effective to attenuate the pulses and smooth the gas flow. Such a combination may provide an attenuation factor in the order of 80%. For further attenuation, as shown in FIG. 1 a second surge damper 11 and back pressure valve 20 are located downstream of the first. The surge damper 11 is of similar construction to the combined mixing chamber and surge damper 8, and is mounted in back-to-back relationship therewith to the connecting plate 20. The surge damper 11 includes a damping piston and rolling diaphragm which although not shown in FIG. 2 are similar to the piston 23 and diaphragm 27 of the combined mixing chamber and surge damper 8. The surge damper 11 includes only a single inlet 61 and an outlet 32 which are again formed as bores in the common connecting plate 20. It should be noted that the gas pressure in the combined mixer and surge damper 8 will be twice that in the surge damper 11, since the effects of the valves 9 and 10 are additive. Therefore in order to match the surge damper 11 to the operating pressure, the piston thereof is biased by only a single coil spring of similar rate to springs 24,25.

Figure 4:
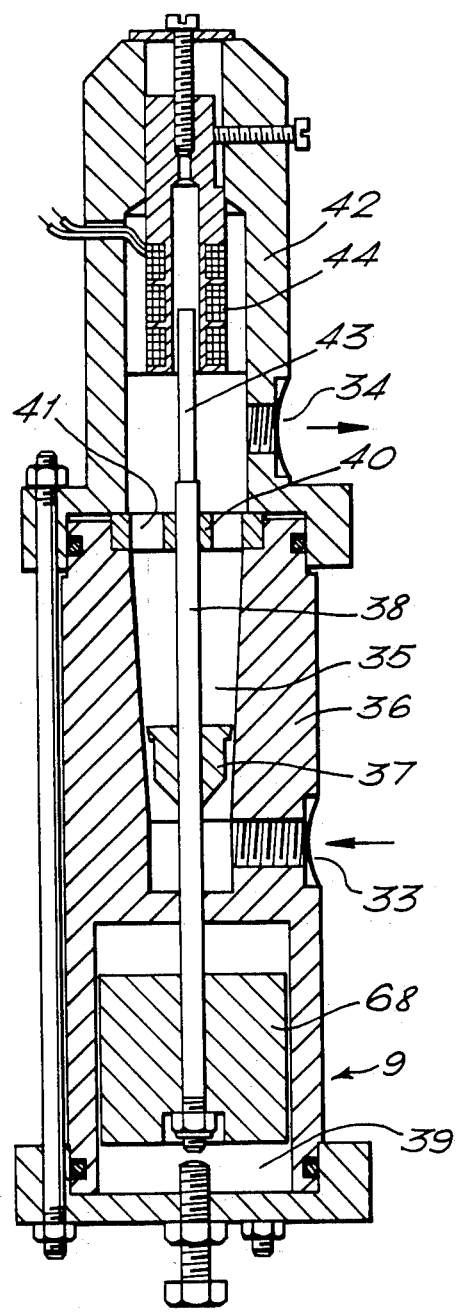
FIG. 4 is a sectional view illustrating a preferred physical layout of the apparatus of FIG. 1.

Referring now to FIG. 4, details of the constant back pressure valve 9 are illustrated. The valve 9 includes an inlet 33 and an outlet 34 connected by a vertical tapered passage 35 defined by a housing 36. Slidably mounted in the passage 35 is a plunger 38 secured to a shaft 38. The shaft 37 mounts at its lower end a weight 68 which is disposed in a closed chamber 39 in a housing below the passage 35. A bush 40 locates the upper portion of the shaft 38, the bush being provided with gas flow apertures 41. Gas flowing though the passage 35 urges the plunger 37 upwardly until the difference in pressure between the gas below and above the plunger is equal to the pressure resulting from the weight of the plunger and weight assembly. Such a valve has been found to maintain a substantially constant back pressure for gas flows in the range of 2 to 18 liters per minute. The restricted air gap between the outer periphery of the weight 68 and the inner wall of the chamber 39 provides damping for the plunger and prevents unwanted dynamic oscillations of the plunger which can occur with a pulsed gas flow.

The valve 9 further comprises a flow metering device located in a housing 42 secured to the top of the housing 36. The plunger shaft 38 mounts a ferromagnetic stem 43 which extends upwardly through an assembly of coils 44. Measurements of the inductance between the coils are indicative of the vertical displacement of the plunger and therefore the gas flow rate through the valve 9. Measurements are made by applying current to a central one of the coils 44 and measuring the current induced in the other coils. The metering device is included in the upstream rather than the downstream back pressure valve since the flow upstream of the second surge damper 11 is still fluctuating to a degree. This enables an integral measurement to be made of the average flow over a short period of time which minimises the possibility of errors due to for example sticking of the plunger at low flow rates.

As mentioned above, a portion of the smoothed flow of mixed gases from the second back pressure valve 10 is bypassed to an anaesthetic drug vapourising arrangement. The flow rate to the vapouriser selector valves 14,15 is regulated by a further pulsed metering valve 45. The required inlet operating pressure for the valve 45 is maintained by the combination of a booster pump 46 and a relief valve 47. In an alternative arrangement, the bypass line 12 may be connected to the main flow line before the second back pressure valve 10. In this way the pressure in the line 12 is increased and this may be necessary for low flow rates.

Figure 5:
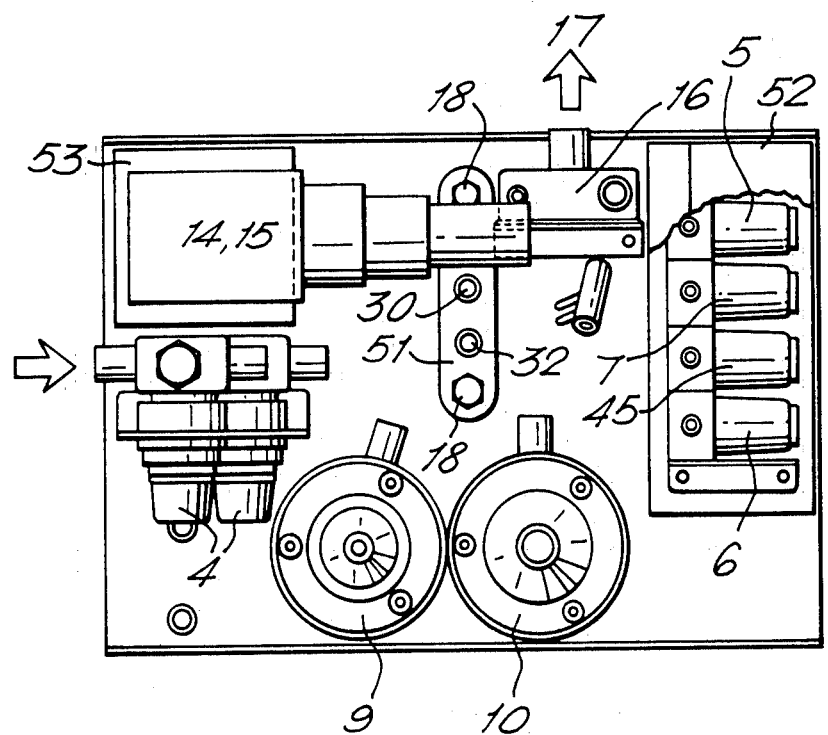

Referring finally to FIGS. 5 and 6, it is illustrated how the various components of the system may be arranged so as to form a compact unit. For reasons of clarity the connecting lines between the individual components have been omitted. The various components are secured to a common mounting plate or tray 50, on the underside of which are located the combined mixer and surge dampers 8,11 and the booster pump 46 and relief valve 47 for the gas flow to the vapourisers. The other components are mounted to the top of the tray 50 which includes an aperture 51 providing access to the inlet and outlet ducts formed in the connecting plate 20 of the mixer and surge damper unit. Thus the aperture also provides access to the outlet jets 18 of the pulsed valves. The solenoid valves 5,6,7,45 are enclosed in a common housing 52 which includes sound insulation; the back pressure valves 9,10 are mounted side by side opposite the second mixing chamber 16, and the inlet regulating valves 4 are secured to a common mounting next to the vapouriser selector valves 14,15. As mentioned above the system lends itself to automatic electronic control, and a printed circuit board 53 for the control circuitry may conveniently be located beneath the vapourised selector valves 14,15.

We claim:

1. Apparatus for mixing and smoothing fluctuating flows of two or more gases, comprising a mixing chamber with at least two inlet ducts and an outlet duct, means for delivering a fluctuating flow of gas to each of said inlet ducts, the mixing chamber including means for absorbing fluctuations in the pressure of the gases therein, and a valve connected to said outlet duct downstream of the chamber for maintaining a substantially constant pressure at said chamber outlet duct.

2. Apparatus as claimed in claim 1 wherein the mixing chamber is cylindrical in cross-section and said inlet ducts are arranged such that the gases enter the chamber tangentially in opposite directions.

3. Apparatus as claimed in claim 1 wherein said means for absorbing fluctuations in gas pressure comprises a spring loaded piston defining a wall of said mixing chamber such piston being outwardly displaceable in response to increases in gas pressure within the chamber.

4. Apparatus as claimed in claim 3 comprising a flexible rolling diaphragm seal adjacent the piston.

5. Apparatus as claimed in claim 1 wherein the value for maintaining a substantially constant pressure at the chamber outlet comprises a variable orifice valve.

6. Apparatus as claimed in claim 5 wherein said valve includes a gravity loaded plunger or float slidably mounted in a vertically disposed, tapered passage through which the gases flow.

7. Apparatus as claimed in claim 6 wherein the float or plunger includes angled slots or channels around its periphery such that the flow of gas thereby produces a rotational torque thereon.

8. Apparatus as claimed in claim 5 wherein the valve has associated therewith means for measuring displacements of said float or plunger which are indicative of the gas flow rate.

9. Apparatus as claimed in claim 8 wherein the float or plunger mounts a ferromagnetic rod which extends to and is movable within an electrical coil means such that changes in inductance of said coil means are indicative of displacements of the rod and thus of the float or plunger.

10. Apparatus as claimed in claim 1 further comprising a surge damper and back-pressure valve arranged in series downstream from said valve for maintaining a substantially constant pressure at the mixing chamber outlet duct.

11. Apparatus as claimed in claim 10 wherein said surge damper comprises a chamber which is cylindrical in cross-section and a spring loaded piston defining a wall of the chamber, the surge damper and the mixing chamber being mounted in back-to-back relationship with a central connecting plate disposed therebetween.

12. Apparatus as claimed in claim 11 wherein gases are transmitted to and from the chambers via conduits formed in the connecting plate.

13. An anaesthesia system comprising apparatus as claimed in claim 1 and further, means connected to said outlet duct for delivering said gas mixture to a patient.

14. A method of mixing and smoothing fluctuating flows of two or more gases comprising introducing two or more fluctuating flows of gases into an enclosed mixing chamber, the mixing chamber including means for absorbing fluctuations in the pressures of the gases therein, and passing the mixed gases through a valve located downstream of the mixing chamber which maintains a substantially constant pressure at the outlet of said chamber.

15. Gas supply apparatus for an anaesthesia system comprising at least two valves and means for controlling said valves to produce pulsed, regulated flows of gases, a mixing chamber having at least two inlets connected to said valves, respectively, downstream of said valves and an outlet, said mixing chamber comprising means in which the gases are mixed, surge damper means in said chamber for attenuating pressure pulses in the mixed gas flow, back pressure valve means connected to said outlet for maintaining a substantially constant back pressure over a wide range of flow rates, anesthetic drug dosing means, means, for directing a controlled proportion of the total gas flow from said back pressure valve means to said anaesthetic drug dosing means, and a second mixing chamber having a first inlet connected to said back pressure valve means and a second inlet connected to said anesthetic drug dosed means for remixing the dose gases with the main gas flow, said second mixing chamber having an outlet adapted to be connected to a patient.

16. Gas supply apparatus as claimed in claim 15 wherein outlet orifices or jets of the respective pulsed valves are mounted so as to be in good thermal communication with one another.

17. Apparatus as claimed in claim 16 wherein the mixing chamber and a surge damping chamber are mounted in back-to-back relationship with a connecting plate disposed therebetween, said outlet orifices or jets being located in orifices formed in said connecting plate.

18. Apparatus as claimed in claim 15 wherein the components are mounted on a common mounting plate or tray.

19. Apparatus for mixing and smoothing a fluctuating flow of two or more gases, comprising a mixing chamber with at least two inlet ducts and an outlet duct, the mixing chamber including means for absorbing fluctuations in the pressure of the gases therein, and a valve connected downstream of the chamber for maintaining a substantially constant pressure at said chamber outlet duct, wherein said mixing chamber is cylindrical in cross-section and said inlet ducts are arranged such that the gases enter the chamber tangentially in opposite directions and wherein said means for absorbing fluctuations in gas pressure comprises a spring loaded piston defining a wall of said mixing chamber said piston being outwardly displaceable in response to increases in gas pressure within the chamber.

20. Apparatus for mixing and smoothing fluctuating flows of two or more gases, comprising a mixing chamber with at least two inlet ducts and an outlet duct, means for delivering a fluctuating flow of gas to each of said inlet ducts, the mixing chamber including means for absorbing fluctuations in the pressure of the gases therein, and a valve connected to said outlet duct downstream of the chamber for maintaining a substantially constant pressure at said chamber outlet duct, wherein said valve includes a gravity loaded plunger or float slidably mounted in a vertically disposed, tapered passage through which the gases flow and wherein the valve has associated therewith means for measuring displacements of said float or plunger which are indicative of the gas flow rate.

* * * * *